(12) United States Patent
Mishima (10) Patent No.: US 9,907,894 B2
(45) Date of Patent: Mar. 6, 2018

(54) HEMODIALYSIS APPARATUS OPERATING METHOD AND HEMODIALYSIS APPARATUS

(71) Applicant: Shibuya Kogyo Co., Ltd., Kanazawa-shi, Ishikawa (JP)

(72) Inventor: Takashi Mishima, Kanazawa (JP)

(73) Assignee: SHIBUYA KOGYO CO., LTD., Kanazawa-shi, Ishikawa (JP)

( * ) Notice: Subject to any disclaimer, the term of this patent is extended or adjusted under 35 U.S.C. 154(b) by 329 days.

(21) Appl. No.: 14/402,136

(22) PCT Filed: May 29, 2013

(86) PCT No.: PCT/JP2013/064849
§ 371 (c)(1),
(2) Date: Nov. 19, 2014

(87) PCT Pub. No.: WO2013/180154
PCT Pub. Date: Dec. 5, 2013

(65) Prior Publication Data
US 2015/0129498 A1    May 14, 2015

(30) Foreign Application Priority Data
May 30, 2012 (JP) .................................. 2012-122656

(51) Int. Cl.
*A61M 1/16* (2006.01)
*A61M 1/34* (2006.01)
(Continued)

(52) U.S. Cl.
CPC ............ *A61M 1/1601* (2014.02); *A61M 1/14* (2013.01); *A61M 1/16* (2013.01); *A61M 1/165* (2014.02);
(Continued)

(58) Field of Classification Search
CPC ........ A61M 1/16; A61M 1/1601; A61M 1/30; A61M 1/3643; A61M 2205/15;
(Continued)

(56) References Cited

U.S. PATENT DOCUMENTS

2013/0150768 A1*  6/2013  Sakamoto et al. ........... 604/6.09
2014/0138301 A1*  5/2014  Iwahori et al. .......... 210/321.72

FOREIGN PATENT DOCUMENTS

JP    2010-184029    8/2010
JP    2011-161060    8/2011
(Continued)

OTHER PUBLICATIONS

International Search Report for PCT/JP2013/064849 (1 page).

*Primary Examiner* — Katherine Zalasky
*Assistant Examiner* — Benjamin Lebron
(74) *Attorney, Agent, or Firm* — Flynn, Thiel, Boutell & Tanis, P.C.

(57) ABSTRACT

A hemodialysis apparatus 1 is provided with a dialyzer 2 for performing hemodialysis, a blood circuit 3 connected to the dialyzer, a dialysis solution circuit 4 connected to the dialyzer, a replacement fluid port 31 provided in the dialysis solution circuit and capable of being opened and closed by a lid member, and a replacement fluid passage 6 having its one end connected to the blood circuit and the other end connected to the replacement fluid port.

4 Claims, 8 Drawing Sheets

(51) Int. Cl.
*A61M 1/36* (2006.01)
*A61M 39/10* (2006.01)
*G01M 3/28* (2006.01)
*A61M 1/14* (2006.01)

(52) U.S. Cl.
CPC ............ *A61M 1/1639* (2014.02); *A61M 1/34* (2013.01); *A61M 1/342* (2013.01); *A61M 1/3431* (2014.02); *A61M 1/3455* (2013.01); *A61M 1/3462* (2013.01); *A61M 1/3465* (2014.02); *A61M 1/3643* (2013.01); *A61M 1/3644* (2014.02); *A61M 1/3649* (2014.02); *G01M 3/2846* (2013.01); *A61M 2039/1077* (2013.01); *A61M 2205/3331* (2013.01); *F04C 2270/0421* (2013.01)

(58) Field of Classification Search
CPC .......... A61M 2205/705; A61M 1/1639; A61M 1/165; A61M 1/3431; A61M 1/3465; A61M 1/14; A61M 1/34; A61M 1/342; A61M 1/3644; A61M 1/3649; A61M 1/3455; A61M 1/3462; A61M 2205/3331; A61M 2039/1077; G01M 3/2846; F04C 2270/0421

See application file for complete search history.

(56) References Cited

FOREIGN PATENT DOCUMENTS

| JP | 2012-005670 | | 1/2012 |
|----|-------------|---|--------|
| WO | WO-2009074588 | A1 * | 6/2009 |
| WO | WO-2012017959 | A1 * | 2/2012 |

* cited by examiner

HEMODIALYSIS APPARATUS OPERATING METHOD AND HEMODIALYSIS APPARATUS

TECHNICAL FIELD

The present invention relates to a hemodialysis apparatus operating method and a hemodialysis apparatus and, more particularly, to a hemodialysis apparatus operating method and a hemodialysis apparatus in which a replacement fluid passage is connected to a dialysis solution circuit when a dialytic treatment is performed.

BACKGROUND ART

Conventionally, hemodialysis is performed with a hemodialysis apparatus causing blood and a dialysis solution to flow through a dialyzer. A blood circuit through which blood is caused to flow and a dialysis solution circuit through which the dialysis solution is caused to flow are connected to the dialyzer.

As such a hemodialysis apparatus, one capable of performing an online hemodialysis filtration treatment (hereinafter referred to as on-line HDF (hemodiafiltration)) by supplying a dialysis solution to a blood circuit during dialytic treatment (Patent Literature 1) is known.

In the hemodialysis apparatus performing the on-line HDF, a replacement fluid passage is provided between the blood circuit and the dialysis solution circuit, and a replacement fluid port for connection to the replacement fluid passage is provided for the dialysis solution circuit. This replacement fluid port can be opened and closed by a lid member.

When preparatory operations for hemodialysis treatment are performed, the replacement fluid port is in the closed state, with the replacement fluid passage detached from the replacement fluid port. In this state, a dialysis solution substitution step to fill the dialysis solution circuit with the dialysis solution is performed. The lid member is thereafter removed from the replacement fluid port and the replacement fluid passage is connected to the replacement fluid port.

PRIOR ART DOCUMENT

Patent Literature

Patent Literature 1: Japanese Patent Laid-Open No. 2011-161060

SUMMARY OF INVENTION

Problem to be Solved by the Invention

In the hemodialysis apparatus having the construction disclosed in Patent Literature 1, the pressure in the dialysis solution circuit is increased as a result of execution of the above-described dialysis solution substitution step, and the dialysis solution overflows to the outside when the lid member is removed from the replacement fluid port, resulting in an unsanitary condition.

In view of this problem, an object of the present invention is to provide a hemodialysis apparatus operating method and a hemodialysis apparatus capable of performing operations in a sanitary manner by preventing overflowing of a dialysis solution.

Means for Solving the Problem

A method of operating a hemodialysis apparatus according to the present invention is a method of operating a hemodialysis apparatus provided with a dialyzer for performing hemodialysis, a blood circuit connected to the dialyzer, a dialysis solution circuit connected to the dialyzer, a replacement fluid port provided in the dialysis solution circuit and capable of being opened and closed by a lid member, and a replacement fluid passage having its one end connected to the blood circuit and the other end connected to the replacement fluid port, in which after a dialysis fluid substitution step of filling the dialysis solution circuit with a dialysis solution, the lid member is detached from the replacement fluid port to change the replacement fluid port from a closed state to an open state, and the replacement fluid passage is connected to the replacement fluid port in the open state, the method including:

performing, after the dialysis fluid substitution step, a negative pressure forming step to make the pressure in the dialysis solution circuit negative so that the dialysis solution does not overflow when the replacement fluid port is opened, and thereafter changing the replacement fluid port from the closed state to the open state.

A hemodialysis apparatus according to the present invention is a hemodialysis apparatus including a dialyzer for performing hemodialysis, a blood circuit connected to the dialyzer, a dialysis solution circuit connected to the dialyzer, dialysis solution flowing means for flowing the dialysis solution in the dialysis solution circuit, control means for controlling the dialysis solution flowing means, a replacement fluid port provided in the dialysis solution circuit and capable of being opened and closed by a lid member, and a replacement fluid passage having its one end connected to the blood circuit and the other end connected to the replacement fluid port in an open state, wherein the dialysis solution flowing means has a construction capable of forming a negative pressure in the dialysis solution circuit under the control of the control means, and wherein the control means makes the pressure in the dialysis solution circuit negative by controlling the dialysis solution flowing means from a state where the replacement fluid port is in a closed state and the dialysis solution circuit is filled with the dialysis solution, thereby enabling prevention of overflowing of the dialysis solution even when the replacement fluid port is opened, and stands by until the replacement fluid port is opened.

Advantageous Effects of Invention

According to the present invention, the pressure in the dialysis solution circuit in which the replacement fluid port is provided is made negative by the negative pressure forming step. Therefore, even in a state where the replacement fluid port is opened when the replacement fluid passage is connected to the replacement fluid port, the dialysis solution in the dialysis solution circuit is drawn into the circuit.

Prevention of overflowing of the dialysis solution from the replacement fluid port can thus be achieved to enable the performing of operations in a sanitary manner.

According to the present invention, the pressure in the dialysis solution circuit is made negative under the control of the control means, thereby enabling prevention of overflowing of the dialysis solution even when the replacement fluid port is opened. Also, this condition is maintained until the replacement fluid port is thereafter opened. Prevention of overflowing of the dialysis solution from the replacement fluid port is thus achieved to enable performing operations in a sanitary manner.

MODE FOR CARRYING OUT THE INVENTION

Figure 1:
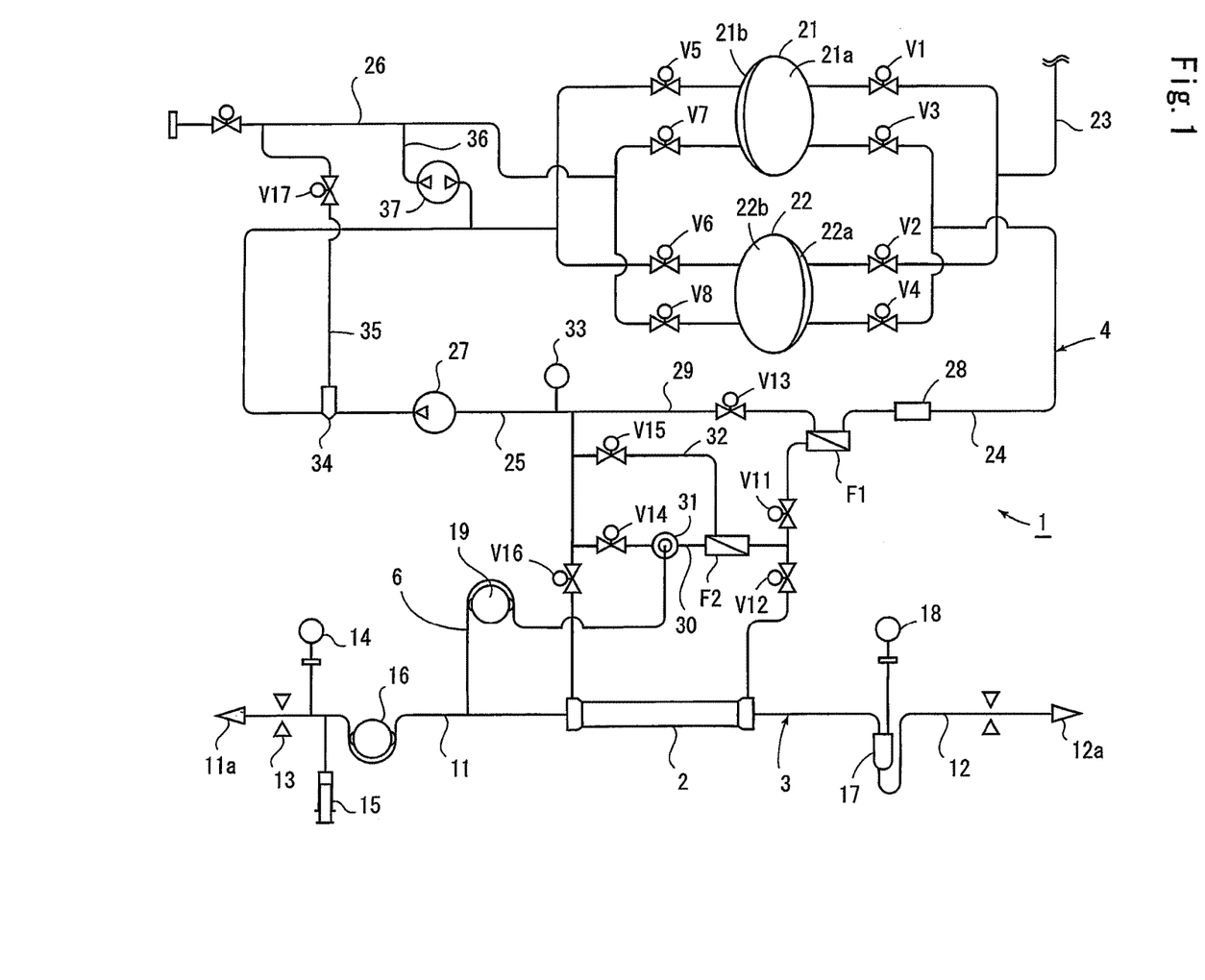
FIG. 1 is a circuit diagram of a hemodialysis apparatus according to the present embodiment.
Figure 2:
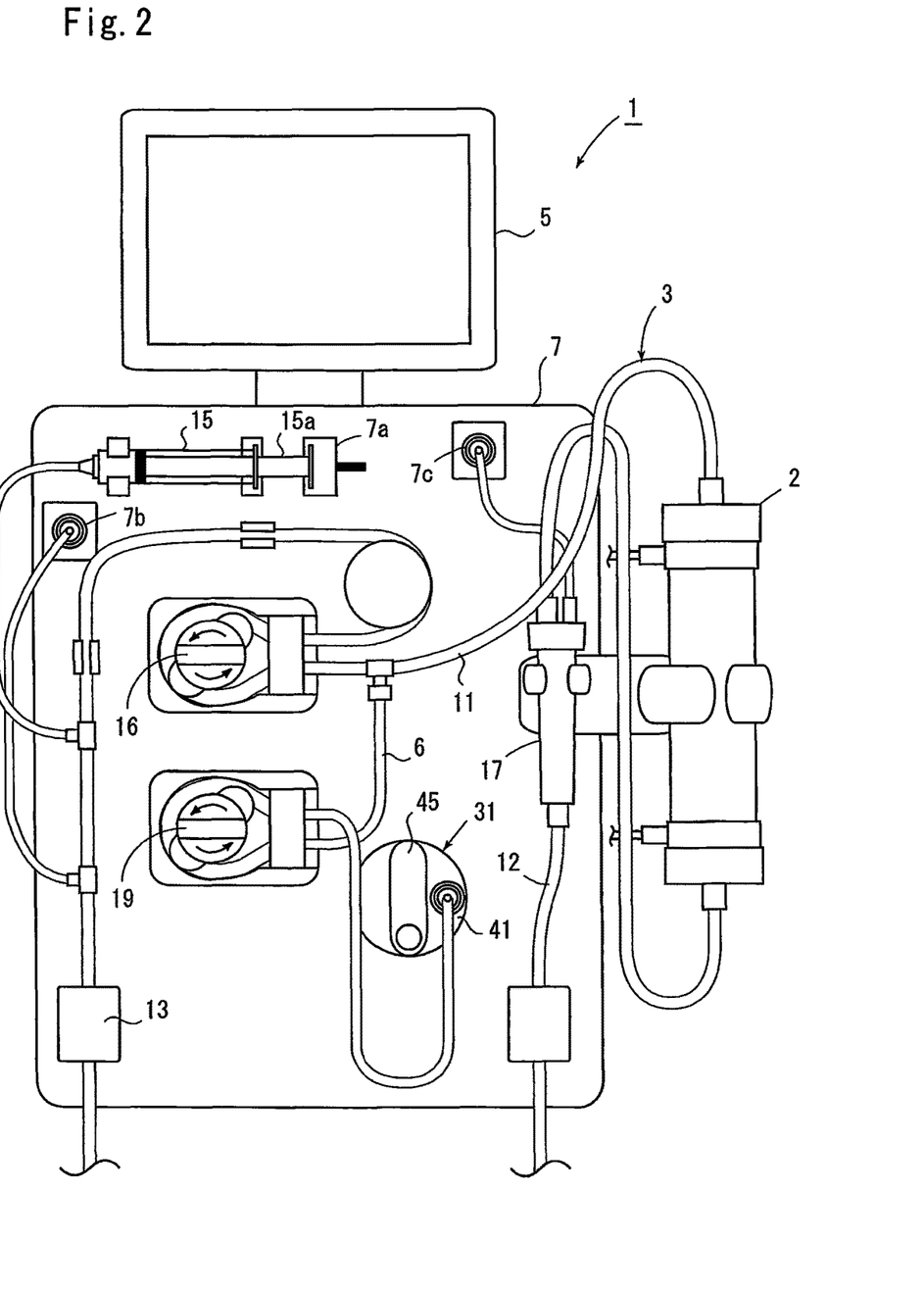
FIG. 2 is a front view of the hemodialysis apparatus.

An embodiment of the present invention will be described below. FIGS. 1 and 2 show a hemodialysis apparatus 1 for performing hemodialysis. FIG. 1 is a circuit diagram and FIG. 2 is a front view.

The hemodialysis apparatus 1 in the present embodiment is provided with a dialyzer 2 with which hemodialysis is performed, a blood circuit 3 connected to the dialyzer 2, and a dialysis solution circuit 4 (not illustrated in FIG. 2) connected to the dialyzer 2. The hemodialysis apparatus 1 is controlled by control means not illustrated and various operations can be performed on the hemodialysis apparatus 1 by means of a touch-panel-type monitor 5 illustrated in FIG. 2.

The hemodialysis apparatus 1 in the present embodiment is capable of performing on-line HDF by supplying a fresh dialysis solution to a patient through the blood circuit 3 and is provided with a replacement fluid passage 6 branching off from the blood circuit 3 and capable of being connected to the dialysis solution circuit 4.

The construction of the hemodialysis apparatus 1 described in the description of the present embodiment is known per se and a method of operating the hemodialysis apparatus 1 according to the present invention can be carried out with such a known hemodialysis apparatus 1.

The dialyzer 2 is vertically held on a side surface of a main body 7, as shown in FIG. 2. The interior of the dialyzer 2 is partitioned into a blood chamber and a dialysis solution chamber by a hollow fiber membrane not illustrated. Blood flows in the blood chamber in a top-to-bottom direction as viewed in the figure, while the dialysis solution flows in the dialysis solution chamber in a bottom-to-top direction as viewed in the figure.

The blood circuit 3 is provided with an artery-side passage 11 connected to an artery of a patient and to an upper end of the dialyzer 2, and a vein-side passage 12 connected to a vein and to a lower end of the dialyzer 2. The replacement fluid passage 6 is connected so as to branch off from the artery-side passage 11.

On the artery-side passage 11, a puncturing needle 11a to be inserted in a patient, clamp means 13 for opening/closing the artery-side passage 11, a pressure gage 14 for measuring pressure (not illustrated in FIG. 2), a syringe 15 containing a blood coagulation preventive agent and a blood pump 16 constituted by a tube pump (peristaltic pump) for feeding blood are provided.

The syringe 15 is attached to the main body 7, and pressing means 7a for pressing a plunger 15a of the syringe 15 is provided on the main body 7. The blood coagulation agent is supplied into the artery-side passage 11 by the pressing means 7a pressing the plunger 15a.

A drip chamber 17 for removing air from blood and a puncturing needle 12a to be inserted in a patient are provided on the vein-side passage 12. A pressure gage 18 for measuring pressure (not illustrated in FIG. 2) is provided on the drip chamber 17.

Referring to FIG. 2, the pressure gage 14 on the artery-side passage 11 and the pressure gage 18 on the vein-side passage 12 are provided inside the main body 7, and tubes from the artery-side passage 11 and the vein-side passage 12 are respectively connected to pressure ports 7b and 7c respectively communicating with the pressure gages 14 and 18.

The replacement fluid passage 6 is connected to the artery-side passage 11 at a position between the blood pump 16 and the dialyzer 2. The replacement fluid passage 6 is replaced together with the dialyzer 2 and blood circuit 3 each time dialysis treatment is performed.

A coupler 6a (see FIG. 5) for connection to a below-described replacement fluid port 31 provided on the main body 7 is provided on an end portion of the replacement fluid passage 6. A replacement fluid pump 19 constituted by a tube pump like the blood pump 16 is provided on the replacement fluid passage 6.

The replacement fluid passage 6 may alternatively be connected to the vein-side passage 12 according to a judgment made by a doctor in charge.

The dialysis solution circuit 4 is provided with first and second dialysis solution chambers 21 and 22, each of which the dialysis solution is supplied to or discharged from and are identical in shape to each other, a solution feed passage 23 through which the fresh dialysis solution is fed to the first or second dialysis solution chamber 21 or 22, a dialysis solution supply passage 24 through which the fresh dialysis solution is supplied from the first or second dialysis solution chamber 21 or 22 to the dialyzer 2, a dialysis solution recovery passage 25 through which the used dialysis solution having passed through the dialyzer 2 is recovered into the first or second dialysis solution chamber 21 or 22, and a drain passage 26 through which the used dialysis solution is discharged from the first or second dialysis solution chamber 21 or 22 to a drain tank not illustrated. These components are housed in the main body 7.

In the present embodiment, pumps and opening/closing valves constituting the dialysis solution circuit 4 constitute dialysis solution flowing means for causing the dialysis solution to flow through the dialysis solution circuit 4 and are controlled by the above-mentioned control means.

Each of the interiors of the first and second dialysis solution chambers 21 and 22 is partitioned by one diaphragm, thereby forming supply sections 21a and 22a which contain the fresh dialysis solution and the recovery sections 21b and 22b which contain the used dialysis solution.

A solution feed pump which feeds the fresh dialysis solution, and which is not illustrated, is provided on the solution feed passage 23. A downstream portion of the solution feed passage 23 diverges into divergent portions extending in two directions to connect respectively to the supply sections 21a and 22b of the first and second dialysis solution chambers 21 and 22. Solution feed valves V1 and V2 are respectively provided in the divergent portions.

An upstream portion of the dialysis solution supply passage 24 diverges into divergent portions extending in two directions to connect respectively to the supply sections 21a and 22b of he first and second dialysis solution chambers 21 and 22. A coupler 24a (see FIG. 5) to be connected to the dialyzer 2 is provided on a downstream end of the dialysis solution supply passage 24. Supply valves V3 and V4 are respectively provided in the divergent portions.

A coupler 25a (see FIG. 5) to be connected to the dialyzer is provided on an upstream end of the dialysis solution recovery passage 25. A downstream portion of the dialysis solution recovery passage 25 diverges into divergent portions extending in two directions to connect respectively to the recovery sections 21b and 22b of the first and second dialysis solution chambers 21 and 22.

A dialysis solution pump 27 for feeding the dialysis solution is provided on the dialysis solution recovery passage 25 upstream of the divergent portions, and recovery valves V5 and V6 are provided in the divergent portions.

An upstream portion of the drain passage 26 diverges into divergent portions extending in two directions to connect respectively to the recovery sections 21b and 22b of the first and second dialysis solution chambers 21 and 22. A downstream portion of the drain passage 26 is connected to the drawn tank not illustrated. Drain valves V7 and V8 are respectively provided in the divergent portions.

Flowing of the dialysis solution in the above-described dialysis solution circuit 4 will be described. The solution feed pump on the solution feed passage 23 and the dialysis solution pump 27 on the dialysis solution recovery passage 25 are operated. In this state, with respect to the first dialysis solution chamber 21, the solution feed valve VI and the drain valve V7 are opened and the supply valve V3 and the recovery valve V5 are closed.

The fresh dialysis solution then flows from the solution feed passage 23 into the supply section 21a of the first dialysis solution chamber 21 to deform the diaphragm and reduce the capacity of the recovery section 21b. The used dialysis solution contained in the recovery section 21b is thereby discharged to the outside through the drain passage 26.

On the other hand, with respect to the second dialysis solution chamber 22, the supply valve V4 and the recovery valve V6 are opened and the solution feed valve V2 and the drain valve V8 are closed. The used dialysis solution then flows into the recovery section 22b to deform the diaphragm and reduce the capacity of the supply section 22a. The fresh dialysis solution contained in the supply section 22a is thereby flowed through the dialysis solution supply passage 24 to be supplied to the dialyzer 2.

Thereafter, the solution feed valves V1 and V2, the supply valves V3 and V4, the recovery valves V5 and V6 and the drain valves V7 and V8 are alternately opened and closed to supply the fresh dialysis solution from the first or second dialysis solution chamber 21 or 22 to the dialyzer 2 through the dialysis solution supply passage 24 to retrieve the used dialysis solution having passed through the dialyzer 2 to the first or second dialysis solution chamber 21 or 22 through the dialysis solution recovery passage 25, thereby maintaining the flowing of the dialysis solution.

A concentration measurement device 28 for measuring the concentration of the dialysis solution is provided on the dialysis solution supply passage 24 downstream of the divergent portions. A first dialysis solution filter F1 for removing detrimental ingredients in the dialysis solution and first and second opening/closing valves V11 and V12 are also provided in the dialysis solution supply passage 24. The first and second opening/closing valves V11 and V12 are provided by being spaced apart by a predetermined distance from each other.

The first dialysis solution filter F1 is partitioned into an upstream section and a downstream section by a semipermeable membrane. When the dialysis solution permeates through the semipermeable membrane from the upstream section into the downstream section, the semipermeable membrane removes detrimental ingredients.

A first bypass passage 29 for communication between the dialysis solution supply passage 24 and the dialysis solution recovery passage 25 is connected to the upstream section of the first dialysis solution filter F1. A third opening/closing valve V13 is provided in the first bypass passage 29.

A second bypass passage 30 for communication between the dialysis solution supply passage 24 and the dialysis solution recovery passage 25 is connected to a point between the first and second opening/closing valves V11 and V12. In the second bypass passage 30 are provided in order from the upstream side a second dialysis solution filter F2, the replacement fluid port 31 connected to the replacement fluid passage 6 and a fourth opening/closing valve V14.

The second dialysis solution filter F2 is also partitioned into an upstream section and a downstream section by a semipermeable membrane, as is the first dialysis solution filter F1. A third bypass passage 32 for communication between the dialysis solution supply passage 24 and the dialysis solution recovery passage 25 through the second bypass passage 30 is connected to the upstream section. A fifth opening/closing valve V15 is provided in the third bypass passage 32.

At the time of dialysis treatment, the replacement fluid passage 6 is connected to the replacement fluid port 31, which is described below in detail, and the dialysis solution is supplied into the replacement fluid passage 6. When preparations for dialysis treatment are made, the replacement fluid passage 6 is not connected; the dialysis solution is flowed through the second bypass passage 30 without being supplied into the replacement fluid passage 6.

In the dialysis solution recovery passage 25 there are provided in order from the dialyzer 2 side a sixth opening/closing valve V16, a pressure sensor 33 for measuring pressure, the dialysis solution pump 27 for feeding the dialysis solution and a deaeration tank 34 for removing air in the dialysis solution.

A downstream end portion of the first bypass passage 29 is connected at a position adjacent to the upstream side of the pressure sensor 33; a downstream end portion of the second bypass passage 30 is connected at a position adjacent to the downstream side of the sixth opening/closing valve V16; and a downstream end portion of the third bypass passage 32 is connected between the first bypass passage 29 and the second bypass passage 30.

On the deaeration tank 34 described below in detail, a fourth bypass passage 35 for communication between the dialysis solution recovery passage 25 and the drain passage 26 is provided. A seventh opening/closing valve 17 is provided on the fourth bypass passage 35.

A fifth bypass passage 36 for communication between the dialysis solution recovery passage 25 and the drain passage 26 is further provided downstream of the deaeration tank 34. A water removal pump 37 for removing water when dialysis treatment is performed is provided on the fifth bypass passage 36.

Figure 3:
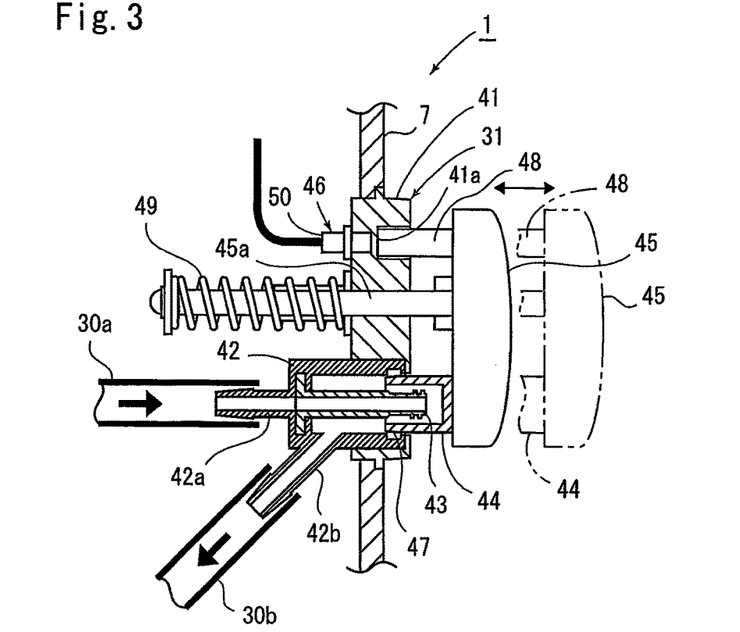
FIG. 3 is a sectional view of a replacement fluid port.

The replacement fluid port 31 provided in the second bypass passage 30 will be described with reference to FIG. 3. Referring to FIG. 3, the replacement fluid port 31 is in a state of being closed with a lid member 44 described below, with the replacement fluid passage 6 not connected thereto.

The replacement fluid port 31 has a base member 41 fixed on the main body 7, an outer port 42 in the form of a cylinder closed at its bottom, fixed to the base member 41, an inner port 43 provided in the outer port 42, the lid member 44 which closes the inner port 43 as well as the outer port 42, a lever 45 for moving the lid member 44, and opening/closing detection means 46 for detecting an open/closed state of the lid member 44.

The base member 41 is a member in the form of a disk such as illustrated in FIG. 2. The lever 45 is provided so as to be rotatable on a through hole formed approximately at a center of the base member 41.

The outer port 42 is provided so that its bottom surface faces in a lateral direction and is fixed so as to open at an end surface of the base member 41. A ring seal 47 in which the lid member 44 is fitted is provided in a distal end portion of an inner circumferential surface of the outer port 42.

A flow inlet 42a to which upstream piping 30a constituting the second bypass passage 30 is connected is formed outside the bottom surface of the outer port 42. A discharge outlet 42b to which downstream piping 30b constituting the second bypass passage 30 is connected is formed below an outer circumferential surface of the outer port 42.

The inner port 43 is a tubular member provided coaxially with the outer port 42. A base portion of the inner port 43 is fixed on a bottom surface of the outer port 42 and communicates with the flow inlet 42a.

A distal end of the inner port 43 projects out of the main body 7 from the outer port 42. A helical groove for connection of the coupler 6a of the replacement fluid passage 6 is formed in an outer circumferential surface of the inner port 43.

The lid member 44 has the shape of a cylinder closed at its bottom. In a closing state illustrated in FIG. 3, an outer circumferential surface of the lid member 44 is maintained in close contact with the ring seal 47 provided in the inner circumferential surface of the outer port 42, thereby forming a space in the outer port 42 and the lid member 44.

In this closing state, a gap is formed between the inner port 43 and the lid member 44, thereby enabling the dialysis solution discharged from the inner port 43 to flow through the space formed by the lid member 44 and the outer port 42 to be discharged out of the discharge outlet 42b.

That is, in the replacement fluid port 31 in the state of being closed with the lid member 44, the dialysis solution having flowed into the upstream piping 30a of the second bypass passage 30 passes through the space formed by the lid member 44 and the outer port 42 and is discharged through the downstream piping 30b and fed into the dialysis solution recovery passage 25.

Conversely, when the replacement fluid passage 6 is connected to the inner port 43 in the open state after removing the lid member 44 from the outer port 42, the opening portion of the outer port 42 is exposed to the outside and the dialysis solution flows from the inner port 43 into the replacement fluid passage 6 and flows into the artery-side passage 11 of the blood circuit 3.

The lever 45 is pivotally supported by a rod 45a provided approximately at a center so as to be rotatable relative to the base member 41. The lid member 44 is fixed on the lever 45 at one end of the same, and a pin 48 is provided on an end portion of the lever 45 at the opposite side.

The rod 45a passes through the base member 41. A spring 49 is resiliently interposed between a portion of the rod 45a projecting inwardly in the main body 7 and the base member 41. The lever 45 is constantly urged in a direction toward the main body 7 by the spring 49.

Stopper holes 41a each closed at its bottom and adapted to receive the pin 48 and regulate the lever 45 from rotating are formed in two places in the base member 41. The pin 48 is received in one of the stopper holes 41a when the lever 45 is positioned in the closing state shown in FIG. 3.

The other stopper hole not illustrated is formed at a position at which the lever 45 is held at such an angle as not to hinder attachment of the replacement fluid passage 6.

The opening/closing detection means 46 is constituted by a magnet provided on the distal end of the pin 48, which magnet is not illustrated, and a magnetism sensor 50 attached to the base member 41 on the reverse side opposite from the stopper hole 41a.

In the closing state illustrated in FIG. 3, the pin 48 is inserted in the stopper hole 41a, the magnet is close to the magnetism sensor 50, and the state in which the replacement fluid port 31 is closed is recognized by detecting the magnetic force of the magnet with the magnetism sensor 50.

When the lever 45 is turned from the state shown in FIG. 3, the pin 48 is detached from the stopper hole 41a and the magnetic force of the magnet cannot be detected with the magnetism sensor 50. As a result, the state in which the replacement fluid port 31 is open is recognized.

Figure 4:
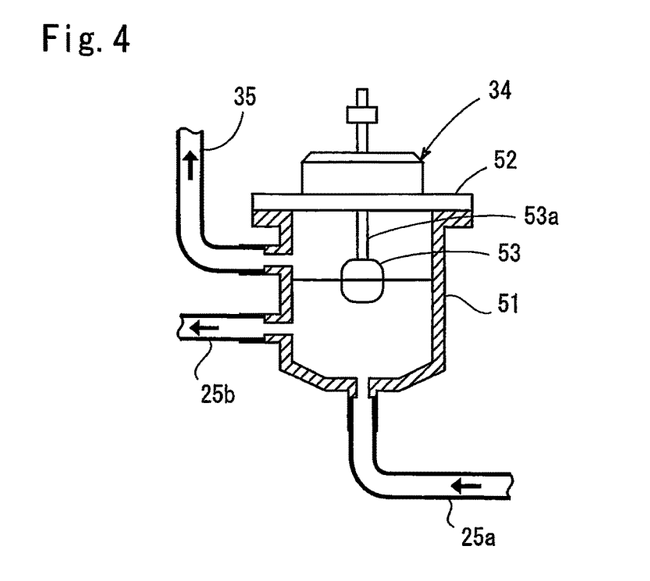
FIG. 4 is a side view of a deaeration tank.

The deaeration tank 34 provided in the dialysis solution recovery passage 25 will be described with reference to FIG. 4. the deaeration tank 34 has a case 51 containing the dialysis solution, a cap 52 tightly closing the case 51 and a float 53 which moves upward or downward by following the liquid level of the dialysis solution in the case 51.

Upstream piping 25a of the dialysis solution recovery passage 25 is connected to a bottom surface of the case 51, and downstream piping 25b of the dialysis solution recovery passage 25 is connected to a side surface higher to some extent than the bottom surface. The fourth bypass passage 35 is also connected at a position higher to some extent than the position of connection of the downstream piping 25b.

A rod 53a passing through the cap 52 and slidable on the cap 52 is provided on the float 53. When the liquid level of the dialysis solution in the case 51 is changed, the float 53 moves upward or downward by following the liquid level.

A contactless switch (not illustrated) is provided on the cap 52. When the liquid level of the dialysis solution in the case 51 is moved downward and when the float 53 is moved apart from the cap 52 by a distance equal to or larger than a predetermined distance, it is recognized by means of the switch that a volume of air equal to or larger than a predetermined volume is contained in the case 51.

When a volume of air equal to or larger than the predetermined volume is contained in the case 51 in dialysis treatment, the contactless switch is operated to open the seventh opening/closing valve V17 in the fourth bypass passage 35, thereby causing the air in the case 51 to be discharged into the drain passage 26 through the fourth bypass passage 35.

The deaeration tank 34 is capable of flowing the dialysis solution through the fourth bypass passage 35 by forcibly flowing the dialysis solution into the case 51 when the seventh opening/closing valve 17 is open, as described below.

The method of operating the hemodialysis apparatus 1 having the above-described construction will be described. A procedure for preparations for dialysis treatment with the above-described hemodialysis apparatus 1 will be described with reference to FIGS. 5 to 8. In each of FIGS. 5 to 8, the color of a circuit attached to each opening/closing valve indicates the open/closed state, the white circle indicating the open state, the black circle indicating the closed state.

The following is assumed unless otherwise noted: the solution feed pump and the dialysis solution pump 27 are operating; the solution feed valves V1 and V2, the supply valves V3 and V4, the recovery valves V5 and V6 and the drain valves V7 and V8 are alternately opened and closed by the control means; and the dialysis solution is being flowed through the dialysis solution flowing means.

Figure 5:
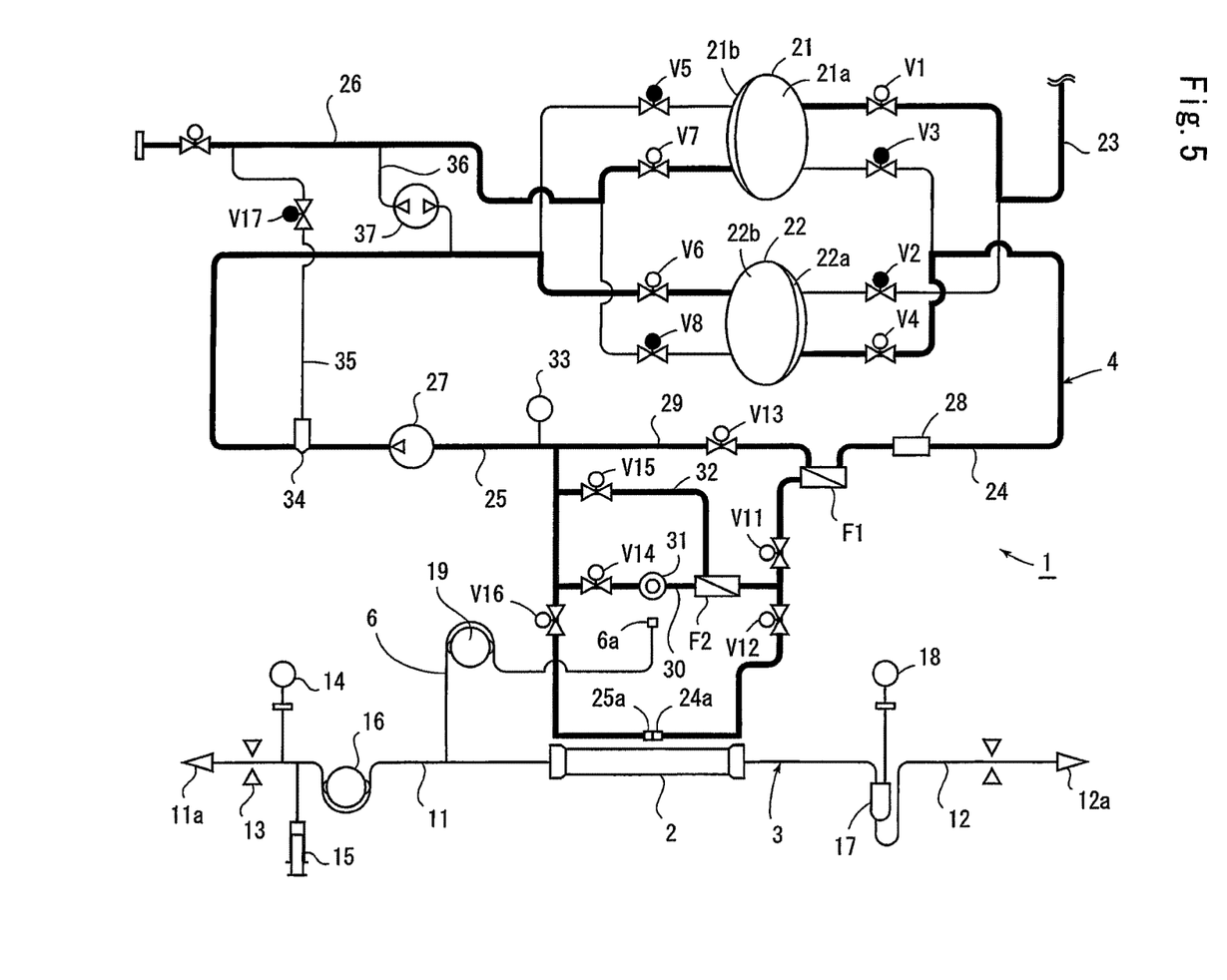
FIG. 5 is a diagram for explaining a dialysis solution substitution step.

FIG. 5 is a diagram for explaining a dialysis solution substitution step of replacing a cleaning liquid filling the dialysis solution circuit 4 with the dialysis solution.

After the completion of preceding dialysis treatment, the dialyzer 2 and the blood circuit 3 are detached from the hemodialysis apparatus 1, and the dialysis solution supply passage 24 and the dialysis solution recovery passage 25 are directly connected to each other by the couplers 24a and 25a.

Since the replacement fluid passage 6 branches off from the blood circuit 3, the replacement fluid passage 6 is detached from the replacement fluid port 31, and the replacement fluid port 31 is closed with the lid member 44.

In this state, the interior of the dialysis solution circuit 4 is cleaned with the cleaning liquid. The interior of the dialysis solution circuit 4 is filled with the cleaning liquid before dialysis treatment is newly performed. This dialysis solution substitution step is a step of replacing the cleaning liquid filling the dialysis solution circuit 4 with the dialysis solution.

This step will be concretely described. The dialysis solution supplied from the first or second dialysis solution chamber 21 or 22 flows through the dialysis solution supply passage 24, passes through the couplers 24a and 25a, and thereafter flows through the dialysis solution recovery passage 25. The cleaning liquid contained in these passages is replaced with the fresh dialysis solution.

Simultaneously, the third to fifth and seventh opening/closing valves V13 to V15 and V17 and the water removal pump 37 are operated as desired to also replace the cleaning liquid contained in the first to fifth bypass passages 29, 30, 32, 35, and 36 with the dialysis solution.

At this time, the replacement fluid port 31 of the second bypass passage 30 is in the closed state and the outer port 42 is closed with the lid member 44. Therefore, the dialysis solution discharged from the inner port 43 fills the space formed by the outer port 42 and the lid member 44.

Therefore, if the lid member 44 is opened when the dialysis solution substitution step is completed, the dialysis solution filling the space formed by the outer port 42 and the lid member 44 overflows to the outside.

In the deaeration tank 34 provided in the dialysis solution recovery passage 25, the interior of the case 51 is also filled with the dialysis solution when the fourth bypass passage 35 is filled with the dialysis solution.

Figure 6:
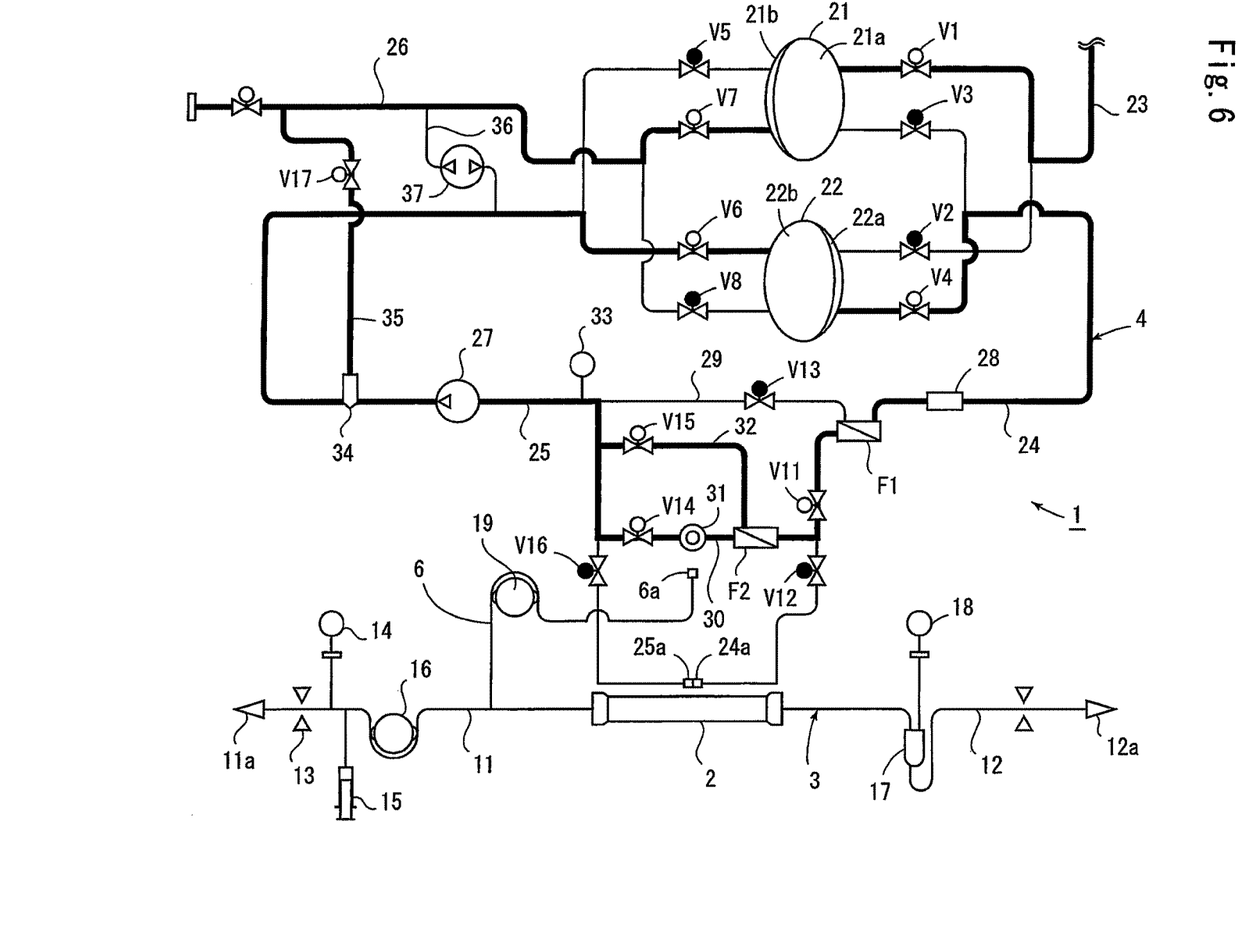
FIG. 6 is a diagram for explaining a negative pressure forming step.

FIG. 6 is a negative pressure forming step of making the pressure in the dialysis solution circuit 4 negative.

Overflowing of the dialysis solution to the outside when the replacement fluid port 31 is opened from the closed state can be prevented by performing this negative pressure forming step and a negative pressure maintenance step described below.

The step will be specifically described. In a state where the dialysis solution is supplied from the first or second dialysis solution chamber 21 or 22, the second opening/closing valve V12 in the dialysis solution supply passage 24, the sixth opening/closing valve V16 in the dialysis solution recovery passage 25 and the third opening/closing valve V13 in the first bypass passage 29 are closed.

On the other hand, the fourth opening/closing valve V14 in the second bypass passage 30 and the fifth opening/closing valve V15 in the third bypass passage 32 are opened to cause the dialysis solution to flow through the second bypass passage 30 and the third bypass passage 32. Further, the seventh opening/closing valve V17 in the fourth bypass passage 35 is opened.

At this time, since the deaeration tank 34 to which the fourth bypass passage 35 is connected is filled with the dialysis solution, the dialysis solution flows from the deaeration tank 34 into the fourth bypass passage 35 and is thereafter discharged into the drain passage 26.

In this way, part of the dialysis solution flowing through the dialysis solution circuit 4 is forcibly discharged from the dialysis solution recovery passage 25 into the fourth bypass passage 35. The pressure in the entire dialysis solution circuit 4 is thereby made negative. The pressure in the second bypass passage 30 in particular is thereby made negative so that the pressure in the space formed by the outer port 42 and the lid member 44 is negative.

When this negative pressure forming step is started, the negative pressure in the dialysis solution passage 25 is measured with the pressure sensor 33 provided on the dialysis solution recovery passage 25. When a negative pressure is reached such that the dialysis solution does not overflow when the replacement fluid port 31 is opened, transition to the subsequent negative pressure maintenance step is made.

If the negative pressure is reduced below the pressure for preventing the dialysis solution from overflowing when the replacement fluid port 31 is opened, there is a risk of external unclean air intruding into the circuit.

The degree of negative pressure described above may be set by experimentally determining a suitable value with reference to factors including the outside diameters of the outer port 42 and the inner port 43.

Figure 7:
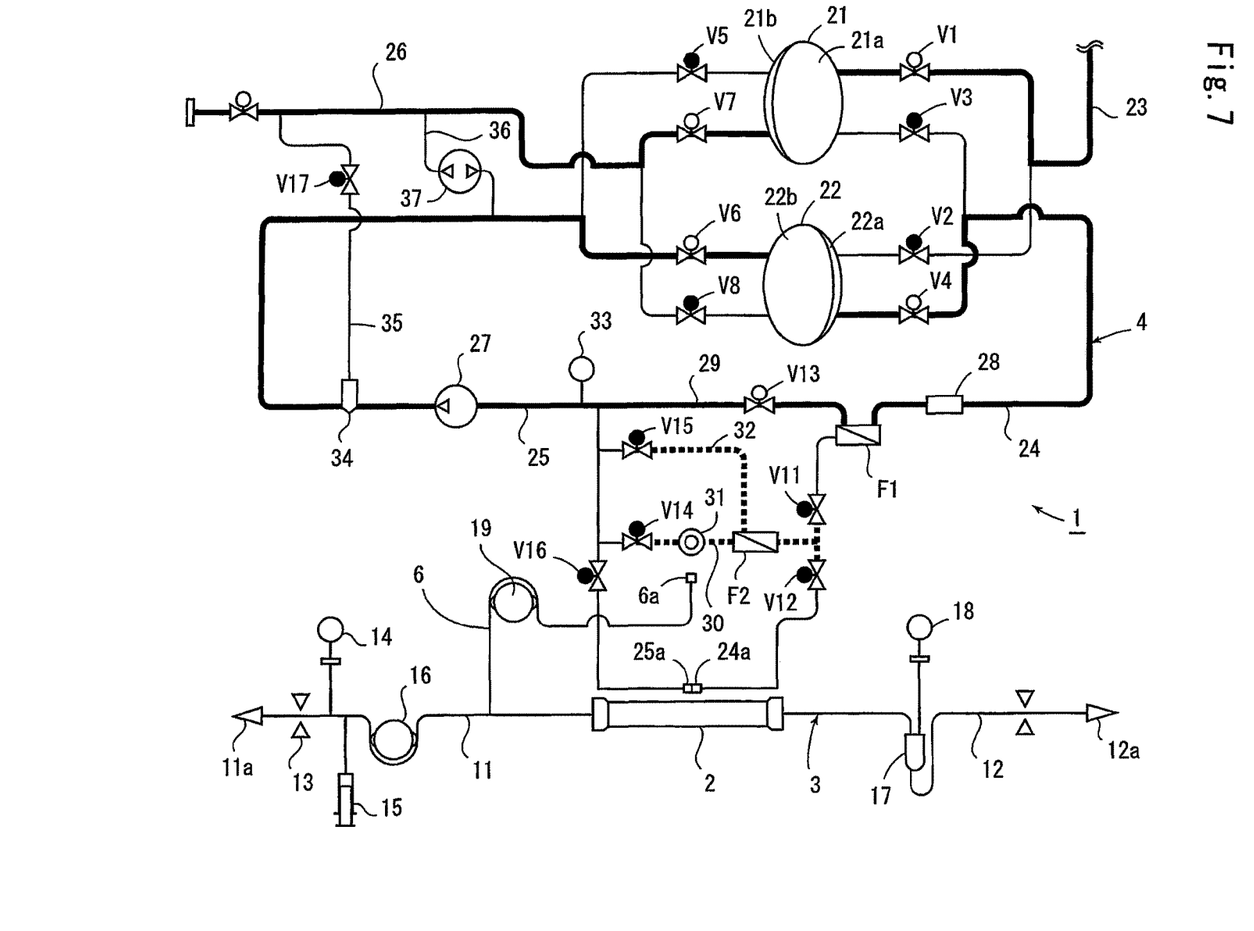
FIG. 7 is a diagram for explaining a negative pressure maintenance step.

FIG. 7 is a diagram for explaining the negative pressure maintenance step of maintaining the negative pressure in the dialysis solution circuit 4.

In this negative pressure maintenance step, the negative pressure condition in the replacement fluid port 31 provided in the second bypass passage 30 having the internal pressure made negative by the above-described negative pressure forming step is maintained until the replacement fluid passage 5 is connected.

More specifically, in contrast with the negative pressure forming step described with reference to FIG. 6, the first, fourth, fifth and seventh valves V11, V14, V15, and V17 are closed and only the third opening/closing valve V13 in the first bypass passage 29 is opened.

As a result, the dialysis solution flows from the dialysis solution supply passage 24 into the dialysis solution recovery passage 25 through the first bypass passage 29. On the other hand, a negative pressure state in which flowing of the dialysis solution is prevented is maintained in the second bypass passage 30 since the adjacent first and second opening/closing valves V11 and V12 and fourth and fifth valves V14 and V15 are closed.

As a result, also in the replacement fluid port 31 provided in the second bypass passage 30, the negative pressure in the space formed by the outer port 42 and the lid member 44 is maintained.

After the completion of this negative pressure maintenance step, the control means notifies the monitor 5 of the state where the replacement fluid passage 6 can be connected to the replacement fluid port 31.

Figure 8:
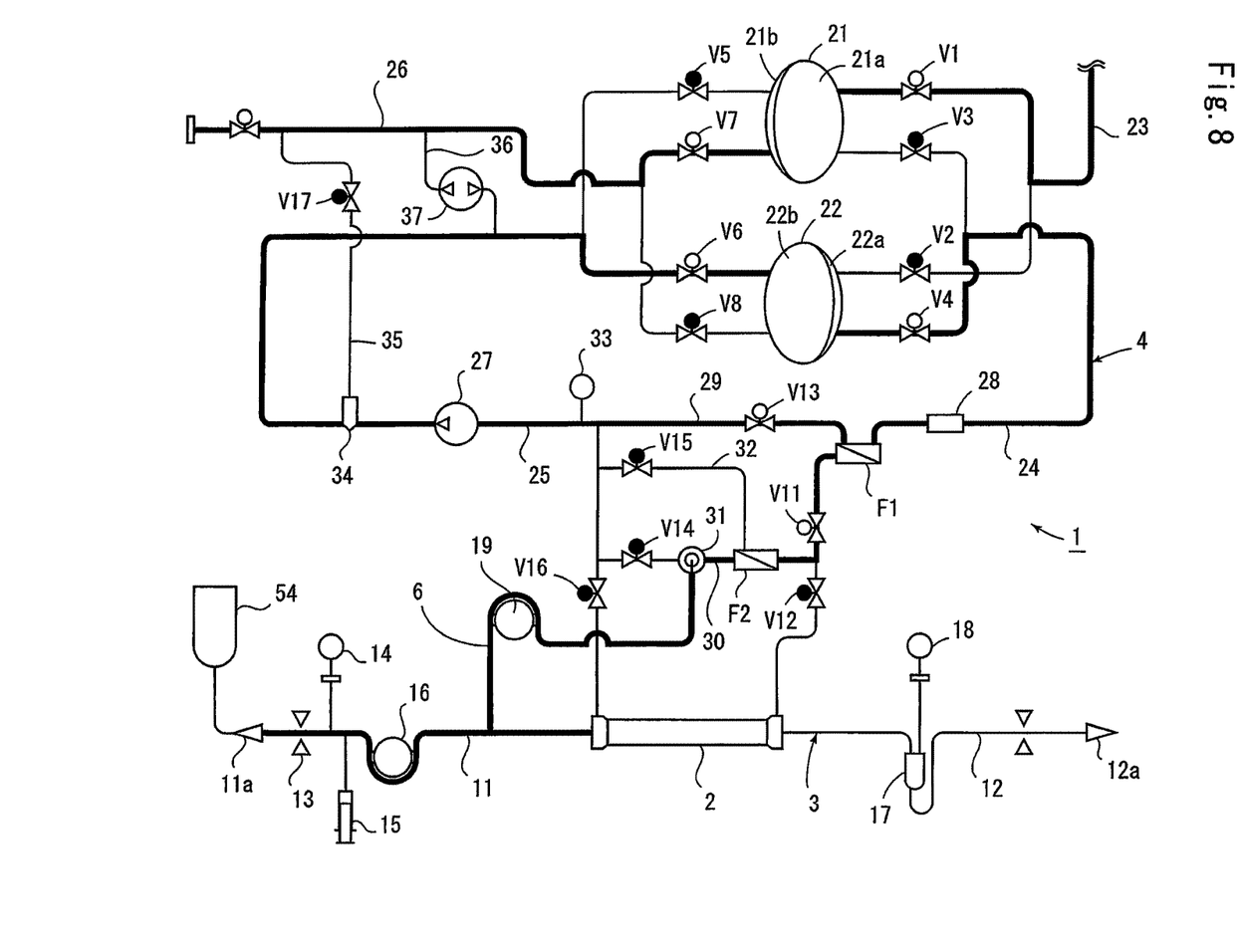
FIG. 8 is a diagram for explaining a replacement fluid passage dialysis solution supply step.

FIG. 8 is a diagram for explaining a replacement fluid passage dialysis solution supply step (priming) of connecting the replacement fluid passage 6 to the replacement fluid port 31 and filling the replacement fluid passage 6 with the dialysis solution.

An operator first attaches the new dialyzer 2 and the blood circuit 3 to the main body 7 and connects the dialysis solution supply passage 24 and the dialysis solution recovery passage 25 in the dialysis solution circuit 4 to the dialyzer 2 by using the couplers 24*a* and 25*a*.

Subsequently, the operator changes the lid member 44 from the closed state to the open state by operating the lever 45 of the replacement fluid port 31 and connects the end of the replacement fluid passage 6 to the replacement fluid port 31.

Since at this time the pressure in the second bypass passage 30 is maintained at a negative value by the negative pressure maintenance step shown in FIG. 7, parts of the dialysis solution in the outer port 42 and the inner port 43 are respectively sucked to the upstream piping 30*a* and downstream piping 30*b* of the second bypass passage 30 even when the lid member 44 is detached from the outer port 42. Therefore, the dialysis solution does not overflow out of the replacement fluid port 31.

After the replacement fluid passage 5 is connected in this way, the first opening/closing valve V11 in the dialysis solution supply passage 24 is opened and the replacement fluid pump 19 is operated in this state, thereby supplying the dialysis solution from the replacement fluid port 31 provided in the second bypass passage 30 into the replacement fluid passage 6 so that the replacement fluid passage 6 is filled with the dialysis solution.

On the other hand, a blood transfusion bag 54 containing physiological saline is connected to the artery-side passage 11 in the blood circuit 3 and the blood pump 16 is operated, thereby filling the blood circuit 3 with physiological saline from the blood transfusion bag 54. The preparations for dialysis treatment are thus completed.

In the above-described embodiment, a negative pressure forming step to make the pressure in the dialysis solution circuit 4 negative is provided after the dialysis solution substitution step to fill the dialysis solution circuit 4 with the dialysis solution, thereby enabling the prevention of the overflowing of the dialysis solution in the replacement fluid port 31 when the replacement fluid port 31, closed with the lid member 44, is opened.

That is, in the dialysis solution substitution step, the dialysis solution circuit 4 has a positive low internal pressure as a result of the feeding of the dialysis solution from the first and second dialysis solution chambers 21 and 22. There is, therefore, a problem that if the replacement fluid port is opened immediately after the dialysis solution substitution step, the dialysis solution is ejected and attached to the main body 7, the floor, etc., and an unsanitary condition results.

In the above-described embodiment, the second bypass passage 30 for communication between the dialysis solution supply passage 24 and the dialysis solution recovery passage 25 is provided and the dialysis solution flows through the second bypass passage 30 when the replacement fluid port 31 is closed.

Even in this arrangement, the pressure in the replacement fluid port 31 can also be made negative by making the pressure in the second bypass passage 30 negative by the above-described negative pressure forming step, thus preventing the dialysis solution from overflowing from the replacement fluid port 31 when the replacement fluid port 31 is opened.

Further, when the negative pressure forming step is performed, the dialysis solution can be discharged through the deaeration tank 34 and the fourth bypass passage 35 used at the time of ordinary dialysis treatment, thus enabling making the pressure in the dialysis solution circuit 4 negative when the well-known hemodialysis apparatus 1 is used.

When the negative pressure forming step is performed, the pressure is measured with the pressure sensor 33 provided on the dialysis solution recovery passage 25. Transition to the negative pressure maintenance step is made after a detection result indicating that the pressure in the dialysis solution circuit 4 has reached a predetermined negative pressure is recognized, thus achieving prevention of an excessive negative pressure in the dialysis solution circuit 4.

The pressure is measured with the pressure sensor 33 and, when a detection result indicating that the pressure in the dialysis solution circuit 4 has reached a predetermined negative pressure is recognized, the monitor 5 is notified of the state where the replacement fluid passage 6 can be connected to the replacement fluid port 31, thus enabling an operator to attach the replacement fluid passage 6 by suitable timing.

Further, when a detection result indicating that the replacement fluid port 31 has been opened is recognized with the magnetism sensor 50, a message to urge the operator to start the replacement fluid passage dialysis solution supply step (priming) can be displayed on the monitor 5 by the control means.

Figure 9:
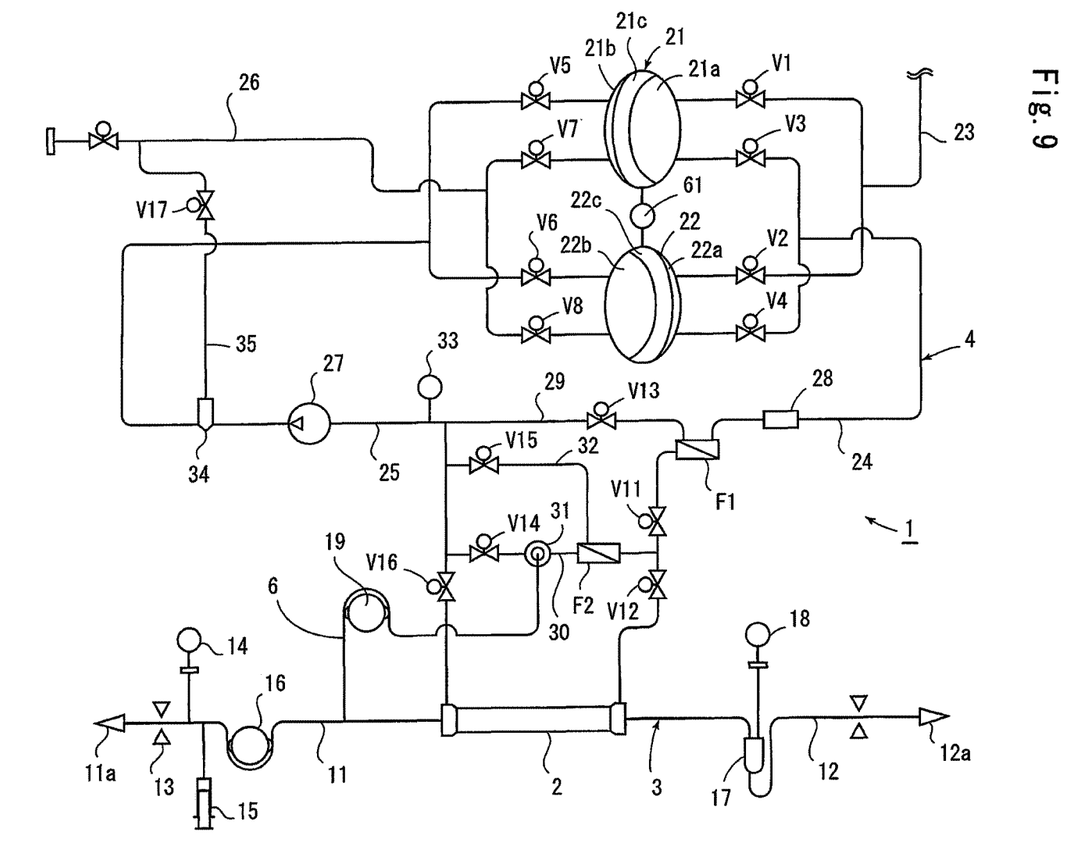
FIG. 9 is a circuit diagram of a hemodialysis apparatus according to a second embodiment.

FIG. 9 is a circuit diagram of a hemodialysis apparatus 1 according to a second embodiment. The same portions as those of the hemodialysis apparatus 1 according to the first embodiment will not be described in the following description.

The hemodialysis apparatus 1 according to the present embodiment has intermediate sections 21*c* and 22*c* containing silicone oil between the supply sections 21*a* and 22*b* and the recovery sections 21*b* and 22*b* in the first and second dialysis solution chambers 21 and 22 constituting the dialysis solution circuit 4, while the fifth bypass passage 36 and the water removal pump 37 in the first embodiment are not provided. The intermediate sections 21*c* and 22*c* are connected to each other by a silicone oil pump 61.

In the hemodialysis apparatus 1 having such first and second dialysis solution chambers 21 and 22, the capacity of one of the intermediate sections 21*c* and 22*c* is reduced by the silicone oil pump 61 provided as the dialysis solution flowing means to produce a negative pressure in the recovery section 21*b* or 22*b* adjacent to the intermediate section, thus enabling removal of water during dialysis treatment.

The hemodialysis apparatus 1 having such a construction is also capable of preventing the dialysis solution from overflowing out of the replacement fluid port 31 provided in the second bypass passage 30 when the replacement fluid passage 6 is connected to the replacement fluid port 31, as is the hemodialysis apparatus 1 in the first embodiment.

More specifically, in the negative pressure forming step to make the pressure in the dialysis solution circuit 4 negative in the first embodiment, the seventh opening/closing valve V17 is opened to cause the dialysis solution to flow through the fourth bypass passage 35. In the present embodiment, however, there is no need to open the seventh opening/closing valve V17.

Instead, the silicone oil pump 61 is operated to reduce the capacity of one of the dialysis solution chambers, thereby producing a negative pressure in the dialysis solution circuit 4. The pressure in the replacement fluid port 31 can be made negative in this way.

In the negative pressure forming step shown in FIG. 6, in the above-described embodiment, the dialysis solution is caused to flow through the fourth bypass passage 35 connected to the deaeration tank 34 provided in the dialysis solution recovery passage 25 to make the pressure in the dialysis solution circuit 4 negative. However, another bypass circuit and an opening/closing valve for opening/closing the bypass circuit may be provided between the dialysis solution recovery passage 25 and the drain passage 26.

In the hemodialysis apparatus 1 removing water by using the water removal pump 37 as in the first embodiment, the water removal pump 37 may be operated in the negative pressure forming step to make the pressure in the dialysis solution circuit 4 negative.

REFERENCE SIGNS LIST

1 Hemodialysis apparatus
2 Dialyzer
3 Blood circuit
4 Dialysis solution circuit
6 Replacement fluid passage
21 First dialysis solution chamber
22 Second dialysis solution chamber
24 Dialysis solution supply passage
25 Dialysis solution recovery passage
27 Dialysis solution pump
30 Second bypass passage
31 Replacement fluid port
35 Fourth bypass passage
42 Outer port
43 Inner port
44 Lid member
V11 to V17 First to seventh opening/closing valves

The invention claimed is:

1. A method of operating a hemodialysis apparatus provided with a dialyzer for performing hemodialysis, wherein a blood circuit is connected to the dialyzer, a dialysis solution circuit is connected to the dialyzer, a replacement fluid port is provided in the dialysis solution circuit and capable of being opened and closed by a lid member, and a replacement fluid passage has an end connected to the blood circuit and another end connected to the replacement fluid port, comprising the steps of:

performing a dialysis fluid substitution step of filling the dialysis solution circuit with a dialysis solution;

performing a negative pressure forming step to make the pressure in the dialysis solution circuit negative so that the dialysis solution does not overflow when the replacement fluid port is opened;

detaching the lid member from the replacement fluid port;

changing the replacement fluid port from a closed state to an open state; and connecting the replacement fluid passage to the replacement fluid port in the open state.

2. The method of operating a hemodialysis apparatus according to claim 1, wherein the dialysis solution circuit includes a dialysis solution supply passage through which the dialysis solution is supplied to the dialyzer, a dialysis solution recovery passage through which the dialysis solution is recovered from the dialyzer, and a bypass passage which provides communication between the dialysis solution supply passage and the dialysis solution recovery passage, and in which the replacement fluid port is provided, the replacement fluid port includes an inner port connected to upstream piping of the bypass passage and an outer port in which the inner port is housed and connected to downstream piping of the bypass passage in fluid communication with the inner port when the replacement fluid port is closed by the lid member, when the replacement fluid port is closed by the lid member, the inner port and the outer port are closed and the dialysis solution discharged from the inner port flows through a space formed by the outer port and the lid member and discharges from the outer port into the downstream piping, and in the negative pressure forming step, the pressure in the replacement fluid port is made negative.

3. The method of operating a hemodialysis apparatus according to claim 1, wherein the dialysis solution circuit includes a dialysis solution recovery passage disposed downstream of the dialyzer, a dialysis solution pump provided in the dialysis solution recovery passage, a bypass passage branching off from the dialysis solution recovery passage downstream of the dialysis solution pump, and an opening/closing valve for opening/closing the bypass passage, and, in the negative pressure forming step, the pressure in the dialysis solution circuit is made negative by the opening/closing valve and causing the dialysis solution in the dialysis solution passage with the dialysis solution pump to flow into the bypass passage that branches in the downstream side of the dialysis solution pump in the dialysis solution recovery passage.

4. The method of operating a hemodialysis apparatus according to claim 1, additionally comprising a negative pressure maintenance step to maintain the pressure in the dialysis solution circuit at a negative pressure at which the dialysis solution does not overflow from the replacement fluid port in an opened state.

* * * * *